United States Patent
Enomoto

(10) Patent No.: US 7,863,575 B2
(45) Date of Patent: Jan. 4, 2011

(54) RADIOGRAPHIC IMAGING METHOD AND RADIOGRAPHIC IMAGING SYSTEM

(75) Inventor: Jun Enomoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 278 days.

(21) Appl. No.: 12/053,572

(22) Filed: Mar. 22, 2008

(65) Prior Publication Data

US 2008/0230708 A1 Sep. 25, 2008

(30) Foreign Application Priority Data

Mar. 22, 2007 (JP) .............................. 2007-074411

(51) Int. Cl.
*G01T 1/24* (2006.01)
(52) U.S. Cl. .................... 250/370.08; 250/363.07; 382/132; 382/275
(58) Field of Classification Search ........... 250/370.08, 250/363.07; 382/132, 275
See application file for complete search history.

(56) References Cited

U.S. PATENT DOCUMENTS

| | | | | |
|---|---|---|---|---|
| 6,118,846 A | * | 9/2000 | Liu | 378/62 |
| 6,296,387 B1 | * | 10/2001 | Guillemaud | 378/207 |
| 6,307,393 B1 | * | 10/2001 | Shimura | 324/765 |
| 6,404,853 B1 | * | 6/2002 | Odogba et al. | 378/98.8 |
| 6,526,366 B1 | * | 2/2003 | Dunton | 702/116 |
| 6,529,618 B1 | | 3/2003 | Ohara et al. | |
| 6,763,084 B2 | * | 7/2004 | Boehm et al. | 378/62 |
| 7,283,165 B2 | * | 10/2007 | Alderson et al. | 348/246 |
| 2001/0031098 A1 | * | 10/2001 | Ford | 382/275 |
| 2004/0252874 A1 | * | 12/2004 | Yamazaki | 382/132 |
| 2007/0065038 A1 | * | 3/2007 | Maschauer et al. | 382/274 |
| 2008/0012967 A1 | * | 1/2008 | Kuwabara | 348/246 |

FOREIGN PATENT DOCUMENTS

| JP | 2000-126162 A | 5/2000 |
|---|---|---|
| JP | 2000-132662 A | 5/2000 |

* cited by examiner

*Primary Examiner*—David P Porta
*Assistant Examiner*—Djura Malevic
(74) *Attorney, Agent, or Firm*—Sughrue Mion, PLLC

(57) ABSTRACT

A radiographic imaging method and system use a radiation solid state detector or a flat panel detector (FPD). The method and system enable radiographic imaging to be continued for a while after occurrence of pixel defects that may lower image quality and minimizing adverse effects of the pixel defects. The pixel defects are analyzed in the respective local regions on the detector. A pixel defect correction is not made on local regions where the pixel defect exceeds a given tolerance but these regions are marked on the radiographic image for recognition.

15 Claims, 5 Drawing Sheets

RADIOGRAPHIC IMAGING METHOD AND RADIOGRAPHIC IMAGING SYSTEM

The entire contents of documents cited in this specification are incorporated herein by reference.

BACKGROUND OF THE INVENTION

The present invention relates to radiographic imaging using a radiation solid state detector and more particularly to a radiographic imaging method and a radiographic imaging system capable of making an efficient use of the radiation solid state detector and displaying proper images though pixel defects in the radiation solid state detector increase over time.

A radiographic image detector has been conventionally used in medicine to produce diagnostic images or in industry for nondestructive tests. The radiographic image detector converts radiation that has penetrated a subject into an electric signal to achieve radiographic imaging. The radiation here includes X-ray, alpha ray, beta ray, gamma ray, electron beam, and ultraviolet ray.

The radiographic image detector is exemplified by a radiation solid state detector, i.e., so-called a flat panel detector hereinafter referred to as FPD, which converts radiation into an electric image signal, and an X-ray image tube that converts a radiographic image into a visible image.

There are two types of FPDs: a direct type and an indirect type. The direct type of FPD collects and reads out electron-hole pairs generated by a photoconductive film such as one formed of amorphous selenium in response to incident radiation, as an electric signal. To be brief, the direct type directly converts radiation into an electric signal. The indirect type has a phosphor layer or a scintillator layer formed of a phosphor that emits light or fluoresces in response to incident radiation to convert radiation into visible light through that phosphor layer, reading out the visible light with a photoelectric transducer. Briefly, the indirect type converts radiation into visible light and the visible light into an electric signal.

One of the causes for image degradation of radiographic images produced by a radiographic imaging system using the FPD is pixel defects of the FPD.

All of the pixels or detecting elements of the FPD do not necessarily produce an output signal with a proper intensity in relation to the amount of incident radiation: some pixels produce an output signal with an abnormally low intensity or an abnormally high intensity in relation to the incident radiation.

Naturally, areas having pixel defects fail to produce proper radiographic image. An image containing such defective areas may cause serious problems such as false or inaccurate diagnoses. In addition, it is impossible to arrest the increase of pixel defects in the FPD that occurs over time.

It is therefore a normal practice with a radiographic imaging system using an FPD to perform pixel detect correction at a given timing whereby the positions of pixel defects of the FPD are detected beforehand at a given timing and, when actually producing a radiographic image, the pixel defects are corrected using data of neighboring pixels according to the pixel defect detection results, so that a radiographic image of which the pixel defects have been corrected may be displayed or printed out by way of reproduction for diagnoses or other purposes.

As the number of pixel defects increases, however, degradation in image quality will necessarily show for all the pixel defect corrections. Notice is therefore preferably given indicating that a given number of pixel defects has been reached or exceeded. Furthermore, it is preferable that the positions where pixel defects are occurring or positions where pixel defects have increased can be correctly recognized to make correct diagnoses or correct interpretation of radiographic images JP 2000-126162 A discloses a radiographic image processing system that outputs both a radiographic image with corrected pixel defects and a radiographic image with uncorrected pixel defects. JP 2000-132662 A discloses a radiographic image processing system that gives a warning when it is judged upon a pixel defect check that pixel defects have increased or additionally occurred by a number judged to have exceeded a given value. The latter system also displays the positions of pixel defects to enable distinction between pixel defects that have additionally occurred and those that were existent previously thereto.

SUMMARY OF THE INVENTION

As mentioned earlier, there are cases where so many pixel defects have occurred that degradation in image quality cannot be adequately compensated for by pixel defect correction to prevent picture quality degradation. Further, when a pixel defect has exceeded a tolerance, pixel defect correction can no loner provide adequate compensation to obtain a radiographic image enabling a correct diagnosis. Such an incorrect radiographic image or diagnostic image can cause serious problems such as false diagnoses.

Accordingly, when pixel defects of the FPD have exceeded a tolerance over which proper pixel defect correction is no longer possible, the FPD, now judged to have reached the end of its service life and be no longer usable, needs to be replaced.

However, when an FPD in a radiographic imaging system is found to contain pixel defects that have exceeded a tolerance and needs to be replaced, a fresh FPD may not be immediately available for replacement. It may take a while before a new FPD becomes available. In addition, FPDs are prohibitively expensive and, therefore, immediate replacement may be impossible for reasons of cost.

Then, a diagnosis using radiographic images is impossible or the only choice left is to make a diagnosis with incorrect radiographic images, which can cause serious problems.

It is an object of the present invention to solve the above problems encountered with said prior art and provide a radiographic imaging method whereby, in radiographic imaging using a radiation solid state detector or an FPD, a correct radiographic image can be obtained by correcting pixel defects of the FPD and, moreover, when pixel defects of the FPD have increased over time, the state of those pixel defects can be correctly known and adverse effects caused by degraded image quality due to the pixel defects can be eliminated to obtain a radiographic image enabling correct diagnosis. It is also an object of the present invention to provide a radiographic imaging system to implement said radiographic imaging method.

Another object of the present invention is to provide a radiographic imaging method, comprising the steps of:

previously analyzing pixel defects in respective predefined local regions of a radiation solid state detector and, further, previously detecting first local regions of the radiation solid state detector in which pixel defects exceeds a given tolerance previously determined; and performing for an acquired radiographic image taken using the radiation solid state detector a pixel defect correction on second image areas of the acquired radiographic image corresponding to second local regions except the first local regions in which the pixel defects exceed the given tolerance previously determined without performing the pixel defect correction on first image areas of the acquired radiographic image corresponding to the first local regions to reproduce a radiographic image.

The radiographic imaging method of the invention preferably comprises the step of, when reproducing the radiographic image, synthesizing onto the radiographic image images indicating the first image areas on which the pixel defect correction has not been performed and which correspond to the first local regions.

Another object of the invention is to provide a radiographic imaging system comprising:

a radiation source;

a radiation solid state detector for detecting radiation radiated by the radiation source;

defect detecting means for detecting pixel defects in the radiation solid state detector;

analyzing means for analyzing the pixel defects detected by the defect detecting means in respective predefined local regions and detecting excess defect regions being first local regions of the radiation solid state detector in which the pixel defects exceeds a given tolerance previously determined; and correcting means for performing for an acquired radiographic image taken using the radiation solid state detector a pixel defect correction on second image areas of the acquired radiographic image corresponding to second local regions except the excess defect regions in accordance with results of pixel defect detection performed by the defect detecting means and results of detection of the excess defect regions performed by the analyzing means.

Preferably, the radiographic imaging system further comprises synthesizing means for synthesizing images indicating first image areas of the acquired radiographic image that correspond to the excess defect regions onto the radiographic image on which the pixel defect correction has been performed by the correcting means.

In the radiographic imaging system, the analyzing means preferably performs a process whereby, when the local regions are regions each having continuous pixel defects, a local region having a number of pixels of the continuous pixel defects not less than a predetermined number is judged as an excess defect region, or a process whereby, when the local regions are regions previously defined on an imaging surface of the radiation solid state detector, a local region containing the pixel defects having a density not lower than a predetermined density is judged as an excess defect region, or both processes.

Preferably, the radiographic imaging system further comprises warning means for giving a warning when the analyzing means detects an excess defect region, and a tentative tolerance having a threshold lower than the given tolerance is set such that the warning means also gives a warning when a local region exceeding the tentative tolerance is detected.

The radiographic imaging system preferably further comprises selecting means for selecting whether or not to perform the pixel defect correction in the excess defect regions and setting means for setting the given tolerances.

Preferably, the local regions previously defined on the imaging surface of the radiation solid state detector are lattice-like regions into which the imaging surface of the radiation solid state detector is divided and in that case, local regions near four corners of the imaging surface of the radiation solid state detector are smaller than other local regions, or the local regions previously defined on the imaging surface of the radiation solid state detector are defined by a movable mask over the imaging surface of the radiation solid state detector.

Further, image data of the acquired radiographic image is preferably related to information indicating existence of the excess defect regions and position information of the excess detect regions.

According to the present invention having the above configuration, pixel defects of the radiation solid state detector are previously detected, and pixel defect correction is basically performed on a radiographic image produced using the radiation solid state detector, making it possible to obtain a high quality radiographic image free from image degradation such as image defects caused by pixel defects.

Further, each of given local regions of the radiation solid state detector is checked for a pixel defect and, when a local region is found to contain a pixel defect exceeding a given tolerance, that local region preferably is allowed to produce image with no pixel defect correction performed thereon, but a warning is given that the radiation solid state detector is reaching the end of its service life while adding information indicating that no pixel defect correction has been performed on that local region. Thus, an observer of the radiographic image produced using a radiation solid state detector having a pixel defect exceeding a tolerance can, aware of the region where a pixel defect has exceeded a tolerance, still make a correct diagnosis free from adverse effects of the pixel defect.

BRIEF DESCRIPTION OF THE DRAWINGS

These and other objects, features, and advantages of the present invention will be apparent from the following detailed description and accompanying drawings in which.

DETAILED DESCRIPTION OF THE INVENTION

Figure 1:
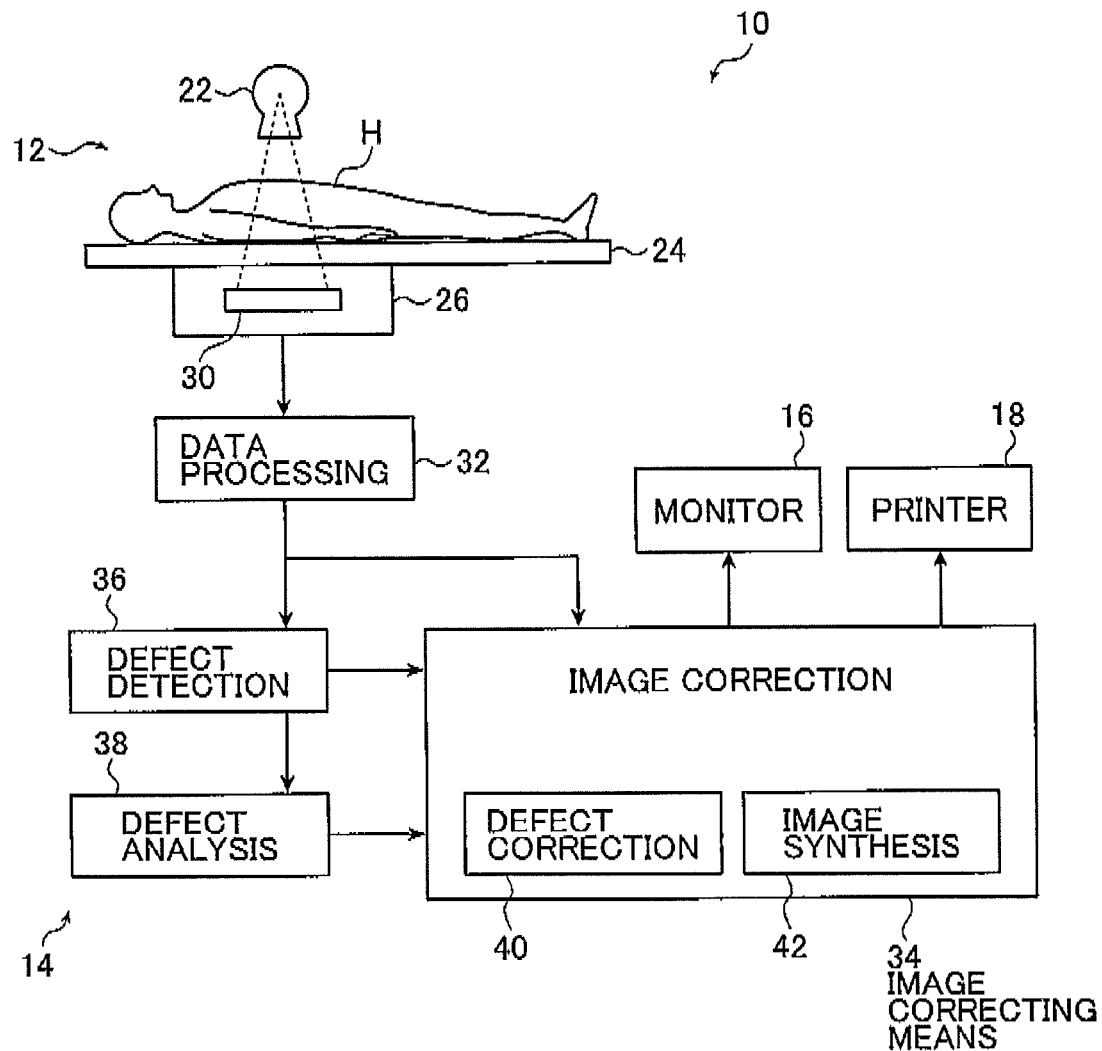
FIG. 1 is a block diagram illustrating the concept of an example of the inventive radiographic imaging system.

FIG. 1 illustrates a concept of an example of the radiographic imaging system to implement the inventive radiographic imaging method.

A radiographic imaging system (hereinafter referred to as imaging system) 10 illustrated in FIG. 1 is a diagnostic radiographic imaging system that produces radiographic images or diagnostic images of a subject H and comprises an imaging unit 12 for producing radiographic images, an image processor 14 for processing a radiographic image produced by the imaging unit 12, a monitor 16, and a printer 18.

The imaging unit 12 is a unit to produce radiographic images of the subject H and comprises a radiation source 22, a radiographic table 24, and imaging means 26.

The radiation source 22 is a normal radiation source installed in various radiographic imaging systems. The radiographic table 24 is a normal radiographic table used with various radiographic imaging systems. The imaging system 10 may, where necessary, comprise moving means for moving the radiation source 22, another moving means for moving the radiographic table 24 vertically and horizontally, and tilting means for tilting the radiographic table 24.

The imaging means 26 produces radiographic images using a radiation solid state detector (referred to below as FPD (flat panel detector)) 30.

As with a normal radiographic imaging system, the imaging system 10 receives radiation that, radiated by the radiation source 22, has passed through the subject H on the light-receptive surface of the FPD 30 and produces a radiographic image of the subject H through photoelectric conversion of the radiation received.

The FPD 30 used in the present invention is a typical FPD used in normal radiographic imaging systems.

According to the present invention, the FPD 30 may be a so-called direct-type FPD or an indirect-type FPD. A typical direct-type FPD, employing a photoconductive film such as one formed of amorphous selenium and a thin-film transistor, collects and reads out electron-hole pairs generated by the photoconductive film in response to incident radiation as an electric signal using the TFT. The indirect-type, employing a scintillator layer formed of a phosphor such as CsI:Tl that emits light or fluoresces in response to incident radiation, a photodiode, a TFT, etc., photoelectrically converts the light emitted by the scintillator layer in response to incident radiation into an electric signal, which is read out using the TFT. The direct-type FPD is preferable in that pixel defects are more liable to increase in the direct-type and hence the effects of the present invention will be manifested in a suitable manner.

Besides the FPD 30, the imaging means 26 may of course comprise other components with which known radiographic imaging systems axe equipped such as a grid for shielding scatter radiation that would otherwise enter the FPD 30 and grid moving means.

The output signal representing a radiographic image produced by the imaging means 26 (FPD 30) is supplied to the image processor 14.

The image processor 14 processes the output signal generated by the FPD 30 to produce image data for the monitor 16 to display, image data for the printer 18 to print, and image data representing radiographic image output that can be used over a network or stored in recording media. In the illustrated imaging system 10, the image processor 14 comprises data processing means 32, image correcting means 34, pixel defect detecting means 36, and pixel defect analyzing means 38.

The image processor 14 may, for example, be configured by one or more computers and workstations and comprises other components than are illustrated, such as a keyboard and a mouse, to perform various operations including entering instructions.

The data processing means 32 performs analog-to-digital conversion, logarithm conversion, etc., on the output signal of the FPD 30 to produce radiographic image data.

The pixel defect detecting means 36 (referred to below as detecting means 36) detects pixel defects in the FPD 30.

As is known, a pixel defect denotes a defect of a pixel (detecting element) that produces an inappropriately high or low output signal in relation to the amount of incident radiation. The detecting means 36 detects pixel defects and produces a defect map that indicates the positions of pixel defects, i.e., positions of defective pixels, in the FPD 30.

The detecting means 36 supplies the defect map it produces to the image correcting means 34 and the pixel defect analyzing means 38 to be described.

According to the present invention, pixel defects may be detected by any of the methods used with various radiographic imaging systems including, without any specific limitations, a method using a darkness image (dark current) and a method using a radiographic image obtained by irradiating or exposing the whole area of the FPD 30 evenly with a given amount of radiation radiated by the radiation source 22 in the absence of the subject H.

The pixel defect analyzing means 38 (referred to below simply as analyzing means 38) analyzes each of predefined local regions in the defect map produced by the detecting means 36 to detect an excess defect region, i.e., a local region containing a pixel defect exceeding a predetermined tolerance.

In the illustrated example, a local region denotes a region containing continuous defective pixels and a given region previously defined on the defect map, i.e., the imaging surface or the light-receptive surface of the FPD 30. The predetermined tolerance denotes dimensions of pixel defects in the case of a region containing continuous defective pixels and a density of pixel defect in the case of a given region defined on the imaging surface. The analyzing means 38 judges a local region to be an excess defect region when the local region contains a pixel defect that exceeds the given tolerance in the dimensions or the density or both.

Figure 2:
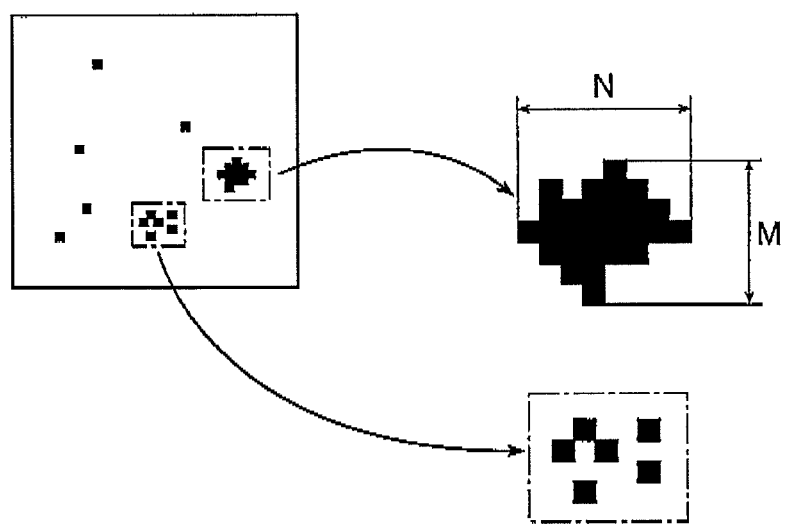
FIG. 2 illustrates a concept of the effects of the inventive radiographic imaging system.

More specifically, the dimensions of a pixel defect denotes dimensions of continuous defective pixels or a cluster of defective pixels, i.e., the number of continuous defective pixels, in the N and the M directions in which pixels are arranged on the FPD 30, as schematically illustrated in FIG. 2. In the illustrated example, the analyzing means 38 judges a local region or a cluster of defective pixels to be an excess defect region when at least one of the dimensions in the N and the M directions exceeds the given tolerance according to a preferred embodiment of the invention. Not only may a local region be judged to be an excess defect region when it contains a pixel defect exceeding the given tolerance in at least one of the N and the M directions, it may also be so judged when the given tolerance is exceeded only in both directions.

The density of a pixel defect denotes the number of defective pixels existing in a given area (mm by mm or pixels by pixels). The analyzing means 38 judges a local region, i.e., a given region previously defined on the defect map, to be an excess defect region when it contains a number of defective pixels exceeding the given tolerance in the given area.

The given area and the area of a local region may be equal or may be different.

The tolerances for the dimensions of a pixel defect and the density of a pixel defect are not limited specifically and may be determined as appropriate according to, for example, the application for which the imaging system 10 is used and the image quality required.

For example, the tolerances may be dimensions and a density beyond which pixel defect correction can no longer enable a radiographic image with sufficient image quality to be obtained, in other words, dimensions and a density of a pixel defect whereby the FPD 30 may be judged to have come to the end of its life or no longer usable.

As will be described, radiographic imaging according to the present invention can be continued even after the occurrence of an excess defect region without performing pixel defect correction in the excess defect region. It follows therefore that a radiographic image subsequently produced may have an image quality that could adversely affect a correct diagnosis if the tolerances are determined according to the life of the FPD 30. To allow for margins, therefore, it is also preferable that the tolerances are set to about 90% to 80% of the dimensions and the density whereby the FPD 30 is regarded to have come to the end of its life.

In addition to the tolerances, tentative tolerance setting lower thresholds than the tolerances, say about 80% of the tolerances, may be provided. Where the tolerances are determined according to the life of the FPD 30, additionally setting the tentative tolerances is effective in ensuring a stable operation of the imaging system.

Further, tolerance setting means may be provided so that a tolerance and, optionally, a tentative tolerance, for the dimensions or the density of a pixel defect or for both may be selected or set. The tolerance setting means may be configured by any known method such as, for example, one of GUI type using the monitor 16, a mouse, a keyboard, etc.

The tolerances may be set steplessly in a given range of say 100% to 60%, or may be set stepwise as in 60%, 70%, etc., where 100% represents the dimensions or the density of a pixel defect reached when the service life ends.

For the same reason as stated above, a maximum of the tolerance is preferably determined allowing for margins in the service life. Alternatively, a maximum of the tolerance may be determined according to the service life such that, when the dimensions or the density of a pixel defect has reached a given value, say 80% of a maximum, a warning is given indicating that the life of the FPD 30 is approaching the end. The warning may be given by a method similar to a method to be described.

The given local region previously defined on the imaging surface of the FPD 30 for detecting the density of defective pixels may also be defined as appropriate in various manners without specific limitations.

Figure 3A:
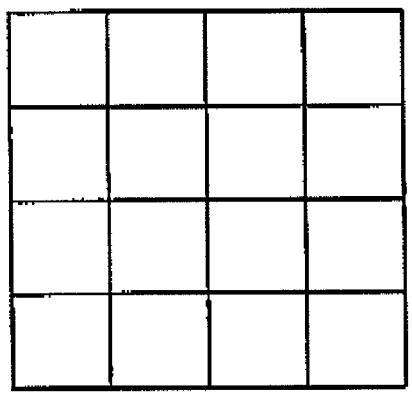
FIGS. 3A, 3B, 3C, and 3D illustrate a concept of the effects of the inventive radiographic imaging system.

For example, the local regions may be block-like regions, comparable to a lattice or a mesh, into which the defect map (imaging surface of the PD 30) is equally divided, as illustrated in FIG. 3A. Considering that the FPD 30 is generally more liable to develop pixel defects at corners thereof, the dimensions of local regions at the corners and, optionally, at the periphery of the FPD 30, may be smaller as illustrated in FIGS. 3B and 3C, instead of providing the local regions all having identical dimensions.

Figure 3B:
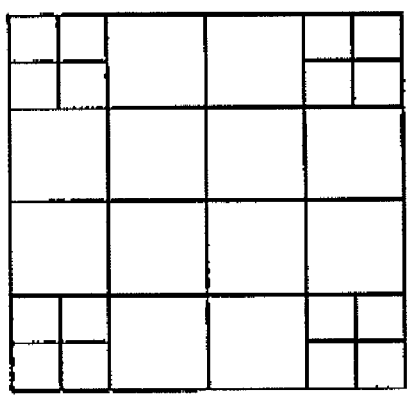
Figure 3C:
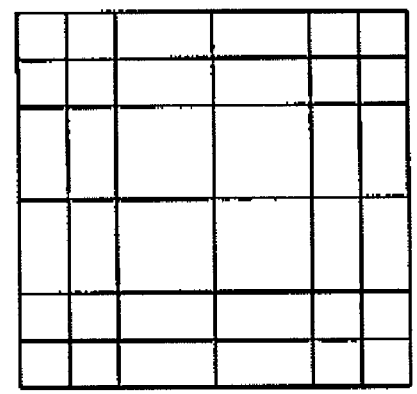
Figure 3D:
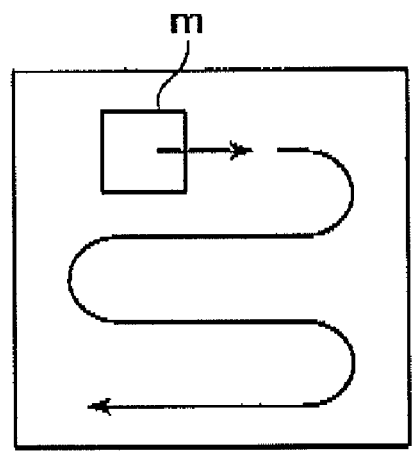

Further, a movable mask "m", a window, having given dimensions may be used to define a local region as schematically illustrated in FIG. 3D instead of fixed local regions. The mask is moved to scan the imaging surface in order to analyze a pixel defect in any given position. In this case, for example, the mask is moved from a given starting position in a given direction; when a pixel defect with a given number of defective pixels is detected in the mask, the mask is stopped in a position where the pixel defect is located at the center of the mask to analyze the pixel defect.

While the methods shown in FIGS. 3A to 3C are preferable in that they are capable of excess defect region detection through quick and easy analyses, these methods can fail to detect a local region that must be judged to be an excess defect region in cases where pixel defects concentrate in a plurality of local regions. By the method shown in FIG. 3D, on the other hand, overlooking such excess defect region may be prevented but analysis of pixel defects takes a long time.

Therefore, which method to use may be determined as appropriate according to the image quality and accuracy required of the imaging system and the processing capabilities, for example, of producing a required number of images in a unit time.

The defect analyzing means 38 analyzes each of such local regions containing continuous defective pixels and regions previously defined on the defect map (imaging surface) for a pixel defect. Upon detecting a local region that contains a pixel defect of which the dimensions or the density or both exceed the tolerances, the defect analyzing means 38 judges that local region to be an excess defect region, acquires or produces position information thereof, and supplies the position information of that excess defect region to the image correcting means 34 or, more specifically, defect correcting means 40 and image synthesizing means 42 to be described. Alternatively, where tentative tolerances are set, a local region that contains a pixel defect of which the dimensions or the density or both exceed the tentative tolerances may likewise be judged to be a tentative excess defect region, acquiring and supplying the position information to the image correcting means 34.

Where the local regions are previously defined on the defect map such as lattice-like blocks into which the defect map is divided, each local region may be assigned a number serving as position information. Thus, the number assigned to a local region judged to be an excess defect region may be supplied to the image correcting means 34 as position information of the excess defect region. In this case, not only position information of the excess defect region containing a pixel defect exceeding the tolerance for the density but also the blocks or regions containing a pixel defect exceeding the tolerance for the dimensions may be used as position information of the excess defect region. To that end, the image correcting means 34 needs to have position information of the local regions corresponding to the numbers assigned to the individual local regions.

Alternatively, coordinates of the pixels located at the opposite corners of an area composed of local regions previously defined on the defect map such as the blocks or coordinates of a rectangle enclosing a pixel defect that exceeds the tolerance for the dimensions may be used to produce such position information of the excess defect region as "a excess defect region defined by a rectangle having opposite angles at $[(n_1-m_1)-(n_2-m_2)]$," which is supplied to the image correcting means 34 as position information of the excess defect region.

Further, the pixel numbers assigned to the individual pixels may be used such that pixel numbers corresponding to a pixel defect are supplied to the image correcting means 34 as defect position information of a pixel defect exceeding the tolerance for the dimensions.

Upon detecting an excess defect region, the defect analyzing means 38 preferably give a warning indicating that the life of the FPD 3 is approaching the end. The warning may be given by any known method: for example, a warning may be displayed on the monitor 16 or a warning may be sounded.

Preferably, the warning is preferably given when at least one excess defect region is detected, to which, however, the present invention is not limited. For example, the warning may only be given upon detecting a number of excess defect regions exceeding a given number that may be determined as appropriate according to, for example, the life of the FPD 30, the applications to which the imaging system 10 is used, and the image quality and accuracy required.

In cases where tentative tolerances are provided, when a tentative excess defect region containing a pixel defect that exceeds a tentative tolerance has occurred, a warning to that effect may be given.

Where the imaging system 10 is connected to a management center of the system, etc., via communication lines, which may be dedicated lines or general communication lines such as the Internet, it is preferable not only to give a warning but also to inform the management center of the occurrence of an excess defect region and, optionally, of a tentative excess defect region, via communication lines, further sending image data of the defect map.

Figure 4:
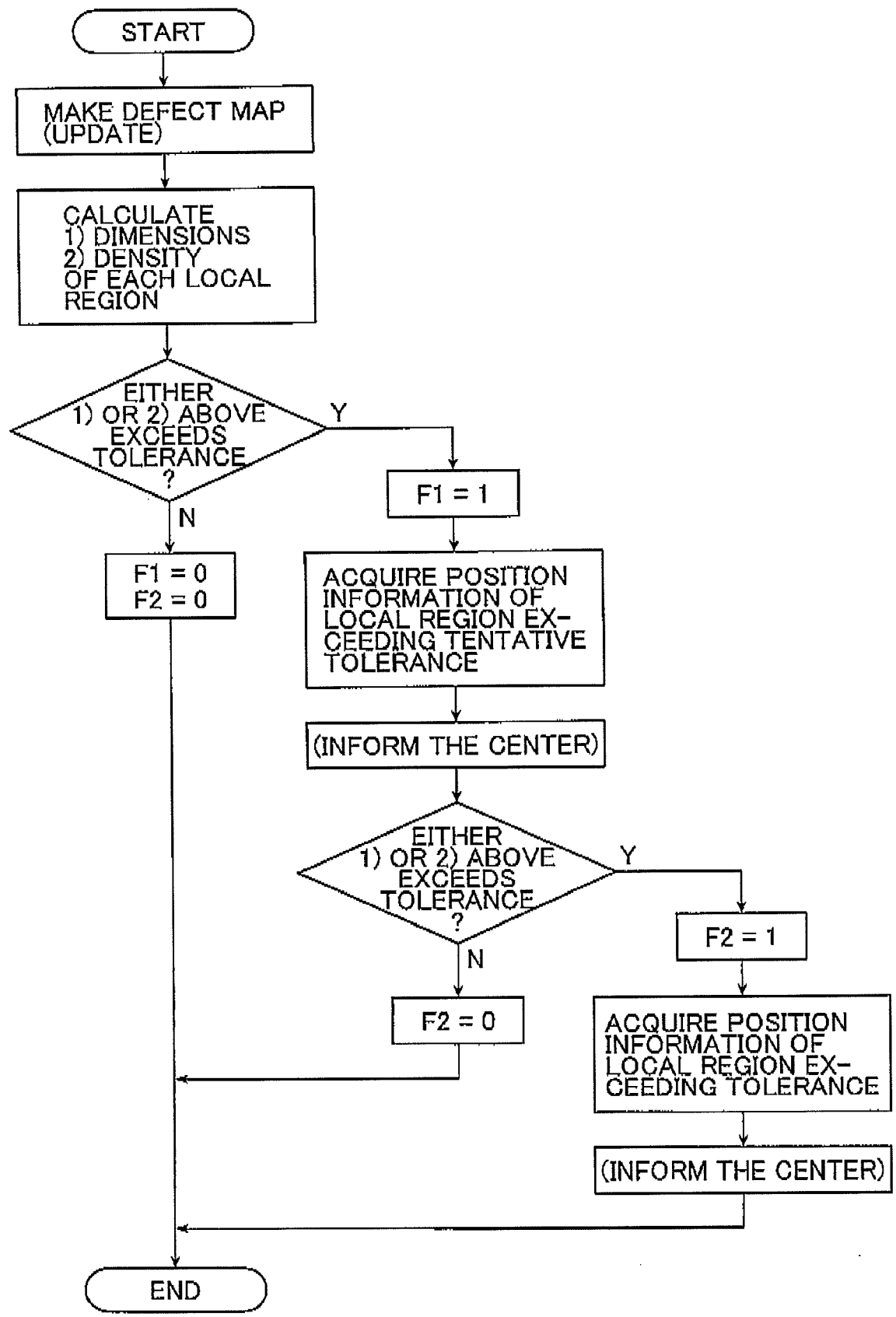
FIG. 4 is a flow chart illustrating the effects of the inventive radiographic imaging system.

Now, detection of an excess defect region performed in the imaging system 10 will be described referring to FIG. 4. The flow chart of FIG. 4 is an example of a case where the tentative tolerances are provided.

Upon the detecting means 36 producing or updating a defect map, the analyzing means 38 analyzes every local region of the defect map, i.e., every region containing continuous defective pixels and every region previously defined on the defect map or the imaging map to determine whether a pixel defect of which the dimensions (1) exceed a tentative tolerance exists and whether a pixel defect of which the density (2) exceeds a tentative tolerance exists.

Detection of pixel defects exceeding the tentative tolerance for the dimensions may be performed by checking each of the regions previously defined on the defect map such as the blocks into which the defect map is divided by the lattice.

The timing at which the detecting means 36 produces or updates a defect map is not limited specifically. Any of the production timings used with various radiographic imaging systems may be employed such as, after the start-up of the imaging system 10, each time imaging is performed a given number of times, each time a given length of time elapses, each time the radiation source 22 radiates a given amount of radiation, or at a timing combining some of these timings.

When it is found, after the pixel defects in all the local regions have been analyzed, that there is no pixel defect of which the dimensions exceed the tentative tolerance and that there is no pixel defect of which the density exceeds the tentative tolerance, which is the case indicated by N in FIG. 4, then flags F1 and F2 are set to 0 on the defect map, thus F1=0 and F2=0.

The flags F1 and F2 corresponds to a tentative tolerance and a tolerance, respectively: 0 indicates that there is no local region exceeding the tolerance or the tentative tolerance, hence, all the local regions are within the tolerances; 1 indicates that there is a local region exceeding the tolerance or the tentative tolerance.

On the other hand, when a local region analyzed is found to contain a pixel defect of which the dimensions or the density or both exceed the tentative tolerance, which is the case indicated by Y in FIG. 4, then the local region is judged to be a tentative excess defect region, setting the flag F1 to 1, thus F1=1, on the defect map.

Further, position information of the tentative excess defect region is acquired and supplied to the image correcting means 34, and, optionally, the management center is informed of the occurrence of the tentative excess defect region in the FPD 30 of the imaging system 10.

Each tentative excess defect region is further analyzed to determine whether the dimensions and density of the pixel defect exceed the tolerances. When all the tentative excess defect regions are found not to exceed the tolerances for both the dimensions and the density, which is the case indicated by N in FIG. 4, then the flag F2 is set to 0, thus F2=0, on the defect map.

On the other hand, when a pixel defect in a tentative excess defect region exceeds the tolerance for the dimensions or the density or both, which is the case indicated by Y in FIG. 4, then the local region is judged to be an excess defect region, setting the flag F2 to 1, thus, F2=1, on the defect map.

Further, position information of that excess defect region is acquired, supplied to the image correcting means 34, and, optionally, the management center is informed of the occurrence of the excess defect region in the FPD 30 of the imaging system 10.

On the defect map, flags may be provided for all the pixel defects such that flags for indicating that the dimensions exceed the tolerance and/or flags for indicating that the density exceeds the tolerance are turned on depending upon whether it is the tolerance for the dimensions or the tolerance for the density that has been exceeded.

The image correcting means 34 performs given processing on the radiographic image, i.e., image data of radiographic image, processed by the data processing means 32 and generates outputs for the monitor 16 to display images and for the printer is to produce hard copies, or outputs that may be placed on the network or in storage media.

The image correcting means 34 in the present invention comprises the pixel defect correcting means 40 and the image synthesizing means 42. The pixel defect correcting means 40 performs pixel defect correction according to the defect map produced by the detecting means 36 showing pixel defects. The image synthesizing means 42 adds an image for indicating an excess defect region to the excess defect region in the radiographic image, producing a composite image.

Note that the image processing performed by the image correcting means 34 is not limited to pixel defect correction and addition of the image for indicating an excess defect region.

The image correcting means 34 is capable of all kinds of image processing performed with various radiographic imaging systems along with pixel defect correction depending on the calibrations, including offset correction (darkness correction) and gain correction (shading correction); tone correction or concentration correction; and data conversion whereby image data is converted into data for the monitor to display or for the printer to print out.

The pixel defect correcting means 40 (referred to below as defect correcting means 40) performs pixel defect correction according to the defect map produced by the detecting means 36.

The pixel defect correction may be performed by any of the methods, without any specific limitation, as used with various radiographic imaging systems including a method whereby an average of neighboring on both sides or peripheral pixels is used as data for the defective pixel and a method whereby the tendency of change of pixels in a given region in the periphery of the pixel defect or data of the pixel defect is generated.

Alternatively, different pixel defects may be corrected by different methods according to the states of the pixel defects such as continuity and density.

The defect correcting means 40 of the inventive imaging system 10 basically corrects all the pixel defects, except that it does not perform pixel defect correction on pixel defects in local regions judged to be excess defect regions according to the position information of the excess defect region supplied by the analyzing means 38.

Expressed otherwise, the defect correcting means 40 in the present invention only performs pixel defect correction on the regions excluding excess defect regions of which the pixel defect exceeds the tolerances. Where the tentative tolerances are provided, the tentative excess defect regions may also be excluded from the regions subject to pixel detect correction as well as the excess defect regions.

A radiographic imaging system using an FPD necessarily suffers increase of pixel defects in the FPD as time passes. Therefore, one needs to be aware of the state of the pixel defects for correct interpretation of the radiographic images. However, when the number of pixel defects has increased significantly, correct radiographic images can no longer be obtained through mere correction of pixel defects. Then, the FPD, which is now considered to have reached the end of its life and be no longer usable, needs to be replaced.

A fresh FPD, however, may not immediately be available in some cases, or timely replacement may be impossible in other cases for reasons of costs as described earlier.

According to studies by the inventor of the present invention, pixel defects do not necessarily occur evenly over its surface but occur locally in many cases.

Thus, even though pixel defects have increased so much that proper pixel defect correction is no longer possible, the regions with such pixel defects often exist only locally. Through pixel defect correction, therefore, the other regions can correctly reproduce a radiographic image.

The present invention focused on this fact. Thus, pixel defects are analyzed locally to know the state of local pixel defects. When it is found that there exists a local region exceeding a tolerance, pixel defect correction is not performed on the local region now found to exceed the tolerance in the radiographic image. When the occurrence of an excess defect region is found, a warning is preferably given indicating that the FPD is approaching the end of its life.

According to the present invention, therefore, even after a point of time when the FPD conventionally would be regarded to be in need of replacement, the user can continue to use the inventive radiographic imaging system for a certain period of time, aware that the FPD is near the end of its life. Further, since pixel defect correction is not performed on excess defect regions, on which proper pixel defect correction cannot be performed, and since images each indicating an excess defect region are preferably added to the radiographic image to produce a composite image, an observer of the radiographic image can correctly recognize the excess defect regions and appreciate the state of the pixel defects thereof to deliver correct diagnoses or make radiograph interpretations such that the adverse effects caused by the pixel defects thus can be reduced to a minimum possible.

Upon occurrence of an excess defect region, an image indicating the excess defect region is added to the radiographic image to produce a composite image. Thus, the observer of the radiographic image can recognize that an excess defect region has occurred and, hence, the FPD is near the end of its life without the warning being given about the approaching end of the life of the FPD.

While pixel defect correction basically is not performed on excess defect regions according to the present invention, there is preferably provided selecting means for performing pixel defect correction on excess defect regions as well. This will enhance the convenience with which the imaging system 10 may be used according to preferences of the observer of the radiographic images, the applications for which the radiographic images are used, convenience of the user of the imaging system 10, and the like.

The selecting means may be configured by a known method such as one of a GUI type using the monitor 16, a mouse, a keyboard, etc.

The selecting means for performing pixel defect correction on an excess defect region may allow the user to select between performing and not performing pixel defect correction depending upon whether it is the dimensions or the density of the pixel defect that has exceeded the tolerance.

Where two or more excess defect regions exist, the selection between performing and not performing the correction may be independently made for the individual excess defect regions.

The image synthesizing means 40 (referred to below as synthesizing means 40) adds an image that enables the observer to recognize an excess defect region to a radiographic image according to position information on the excess defect region supplied from the analyzing means 38 to produce a composite image.

The composite image produced by the synthesizing means 40 may use a variety of images that enable recognition of an excess defect region as exemplified by frame borders such as a black frame border or a white frame border, a double-lined black or white frame border, and a dotted-line black or white frame border to enclose the excess defect region. Where the monitor and the printer used to reproduce radiographic images are a color monitor and a color printer, a color may be synthesized and added to the excess defect region to make the excess defect region recognizable.

Where a pixel defect exceeds a tolerance for the dimensions, the excess defect region is already well recognizable as such on the reproduced image depending upon the tolerance without an image for the recognition of the excess defect region added. Then image synthesis need not necessarily be performed. Further, local regions such as the lattice-like local regions as exemplified by the blocks described earlier defined on the defect map for density analysis may be used to mark an excess defect region containing a pixel defect that exceeds the tolerance for the dimensions by adding an image that enables recognition of the excess defect region.

Where tentative tolerances are provided, image synthesis may be performed in such a manner as to enable recognition of a tentative excess defect region in addition to an excess defect region.

Anticipating cases where a radiographic image containing an excess defect region is outputted to an external computer via a network or other means, or where a radiographic image containing an excess defect region is recorded in recording means such as a CD-R and a USB thumb drive, the image correcting means 34 preferably adds information that the radiographic image contains an excess defect region, information on the excess defect region, information indicating whether pixel defect correction has been done on the excess defect region, or other information to the header, etc., of image data of the radiographic image.

Now, examples of the effects produced by pixel defect correction performed by the defect correcting means 40 will be described referring to the flow chart of FIG. 5 and FIG. 6.

To perform image defect correction, the defect correcting means 40 first reads out a defect map produced by the defect detecting means 36. In this example, which assumes that no pixel defect correction is performed on either a tentative excess defect region or an excess defect region, the flags F1 and F2 on the defect map are checked to see whether F1=0 and F2=0. Where only the excess defect region is excluded from pixel defect correction, then whether F2=0 need only be checked.

Figure 5:
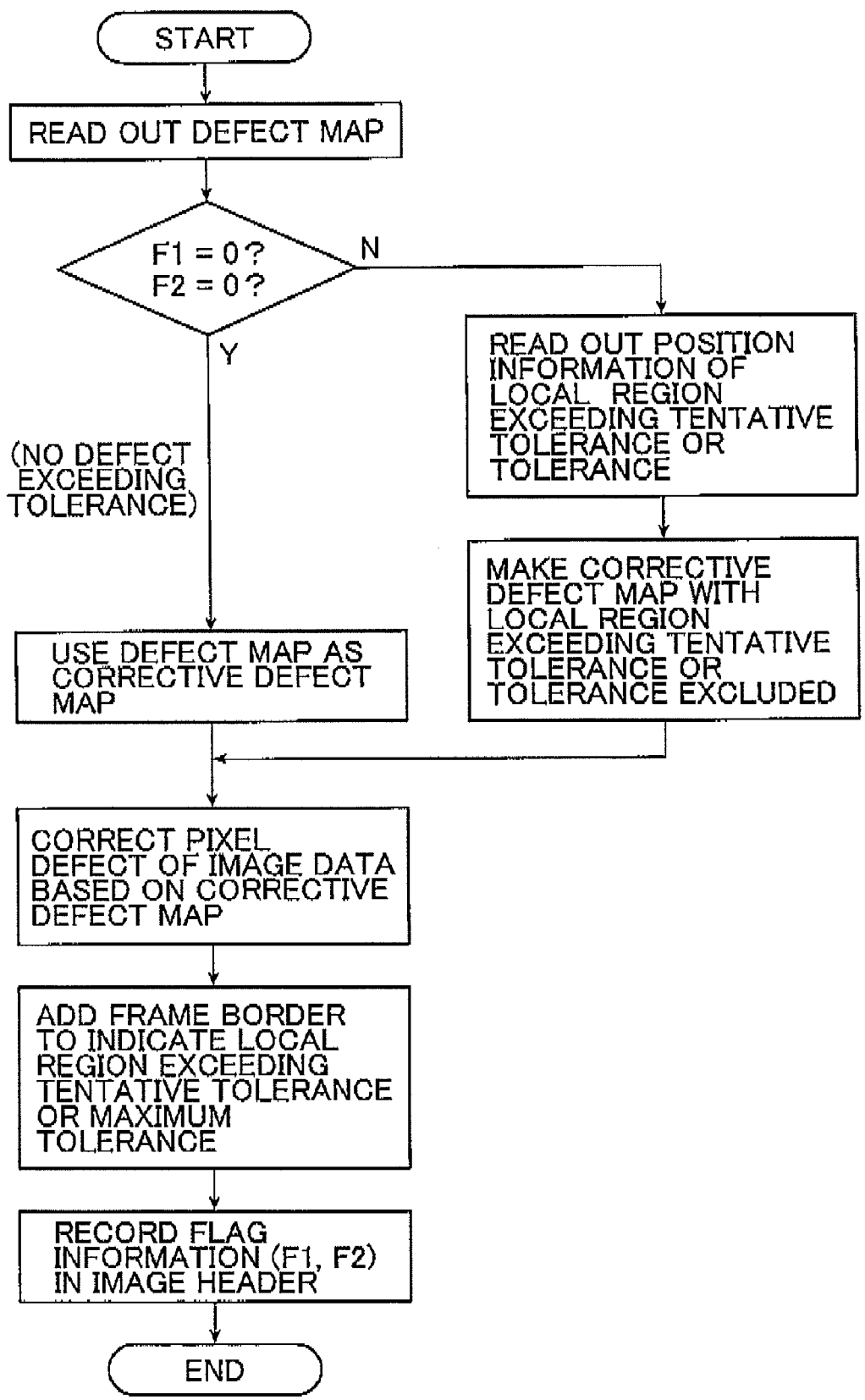
FIG. 5 is a flow chart illustrating the effects of the inventive radiographic imaging system.

When the flags F1 and F2 on the defect map are both 0s, thus, F1=0 and F2=0, which is the case indicated by Y in FIG. 5, then neither a tentative excess defect region nor an excess defect region exists. In this case, the defect map is used intact as a corrective defect map for correcting pixel defects.

When, on the other hand, the flags F1 and F2 on the defect map are not both 0s, thus both F1=0 and F2=0 do not hold at the same time, there exists a tentative excess defect region and/or an excess defect region. Therefore, position information on the local regions containing a tentative excess defect region and an excess defect region is read out.

Subsequently, pixel defects located in the tentative excess defect region and the excess defect region are removed from the defect map to produce a corrective defect map. For example, supposing that the region indicated by a dasheddotted line in FIG. 6E is an excess defect region, the pixel defect in this region is removed from the defect map to produce a corrective defect map.

Subsequently, the defect correcting means 40 uses the corrective defect map to correct the pixel defects indicated on the map. Since, as described earlier, the pixel defects in the tentative excess defect regions and the excess defect regions have been removed from the defect map, the pixel defects existing in such regions in the radiographic image are not subject to correction.

Figure 6A:
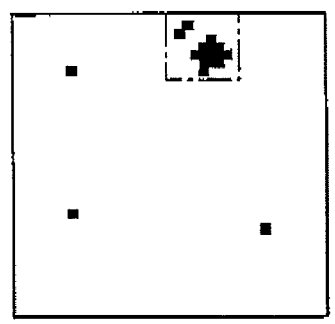
FIGS. 6A, 6B, 6C, 6D, and 6E are flow charts illustrating the effects of the inventive radiographic imaging system.
Figure 6B:
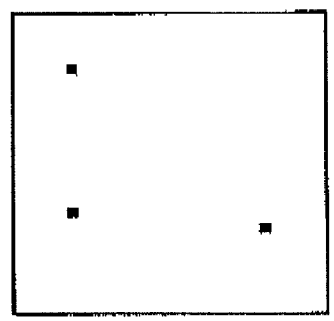
Figure 6C:
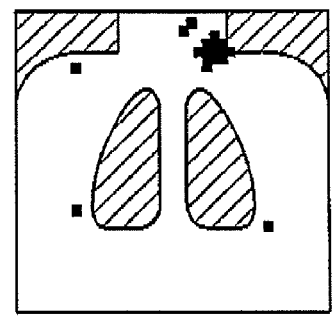
Figure 6D:
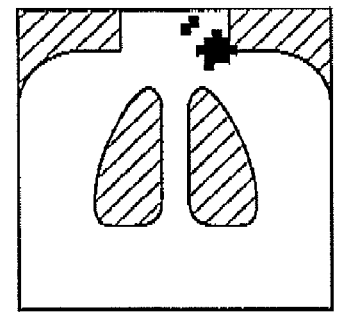

Suppose that there exist excess defect regions, a radiographic image illustrated in FIG. 6C, for example, is corrected using a corrective defect map illustrated in FIG. 6B to produce a corrected image where the pixel defects except those in the excess defect regions are corrected as illustrated in FIG. 6D.

Figure 6E:
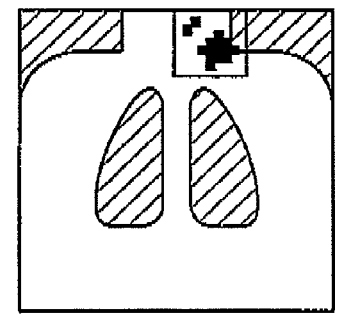

Upon production of the corrected image by the defect correcting means 40, the synthesizing means 42 acquires position information of the local regions found to be a tentative excess defect region and an excess defect region, and adds frame borders onto the radiographic image as illustrated in FIG. 6E.

Further, the image correcting means 34 records information as to, for example, the presence or absence of an excess defect region in the header of the radiographic image data. By way of example, information on the flags F1 and F2 is recorded in the header of the radiographic image in the example under discussion, as indicated in the flow chart of FIG. 5.

While the present invention related to a radiographic imaging method and a radiographic imaging system has been described with reference to specific embodiments, it is to be understood that various changes and modifications may be made without departing from the true spirit and scope of the invention.

What is claimed is:

1. A radiographic imaging method, comprising the steps of:
   previously detecting pixel defects in a radiation solid state detector;
   analyzing the detected pixel defects to judge at least one of a local region having continuous pixel defects not less than a predetermined number of pixels and a local region containing the pixel defects with a density not lower than a predetermined density as an excess defect region; and
   performing for an acquired radiographic image taken using said radiation solid state detector a pixel defect correction on second image areas of said acquired radiographic image corresponding to regions except local regions judged to be excess defect regions without performing said pixel defect correction on first image areas of said acquired radiographic image corresponding to the local regions judged to be the excess defect regions to reproduce a radiographic image.

2. The radiographic imaging method according to claim 1, comprising the step of, when reproducing said radiographic image, synthesizing onto said radiographic image images indicating said first image areas on which said pixel defect correction has not been performed.

3. The radiographic imaging system according to claim 1, wherein lattice-like regions into which an imaging surface of said radiation solid state detector is divided are previously defined as the local regions.

4. The radiographic imaging system according to claim 3, wherein local regions near four corners of said imaging surface of said radiation solid state detector are smaller than other local regions.

5. The radiographic imaging system of according to claim 1, wherein said local regions are on an imaging surface of said radiation solid state detector by a movable mask over said imaging surface of said radiation solid state detector.

6. The method of claim 1, wherein analyzing the detected pixel defects for the predetermined number of pixels or the predetermined density occurs before acquiring a radiographic image of a patient is performed within an imaging cycle for a single patient.

7. The method of claim 1, further comprising issuing a warning regarding a lifetime of the solid state detector according to a result of analyzing the detected pixel defects when the excess defect region is determined to occur in the solid state detector.

8. A radiographic imaging system comprising:
   a radiation source;
   a radiation solid state detector for detecting radiation radiated by said radiation source;
   defect detecting means for detecting pixel defects in said radiation solid state detector;
   analyzing means for analyzing said pixel defects detected by said defect detecting means to judge at least one of a local region having continuous pixel defects not less than a predetermined number of pixels and a local region containing the pixel defects with a density not lower than a predetermined density as an excess defect region; and
   correcting means for performing for an acquired radiographic image taken using said radiation solid state detector a pixel defect correction on second image areas of said acquired radiographic image corresponding to regions except local regions judged to be excess defect regions without performing said pixel defect correction on first image areas of said acquired radiographic image corresponding to the local regions judged to be the excess defect regions in accordance with results of pixel defect detection performed by said defect detecting means and results of detection of said excess defect regions performed by said analyzing means to reproduce a radiographic image.

9. The radiographic imaging system according to claim 8, further comprising synthesizing means for synthesizing images indicating the first image areas of said acquired radiographic image that correspond to said excess defect regions onto said radiographic image on which said pixel defect correction has been performed by said correcting means.

10. The radiographic imaging system according to claim 8, further comprising warning means for giving a warning when said analyzing means judges a local region as an excess defect region.

11. The radiographic imaging system according to claim 10, wherein at least one of a tentative tolerance having a threshold lower than said predetermined number of pixels and a tentative tolerance having a threshold lower than said predetermined density is set, and said warning means also gives a warning when a local region exceeding said tentative tolerance is detected by said analyzing means.

12. The system of claim 10, wherein the analyzing of pixel defects occurs prior to acquiring radiographic image of a patient within an imaging cycle for a single patient.

13. The radiographic imaging system according to claim 8, further comprising selecting means for selecting whether or not to perform said pixel defect correction in image areas of said acquired radiographic image corresponding to said excess defect regions.

14. The radiographic imaging system according to claim 8, further comprising setting means for setting at least one of said predetermined number of pixels and said predetermined density.

15. The radiographic imaging system of according to claim 8, wherein image data of said acquired radiographic image is related to information indicating existence of said excess defect regions and position information of said excess defect regions.

* * * * *